US007192701B2

(12) United States Patent
Lee et al.

(10) Patent No.: US 7,192,701 B2
(45) Date of Patent: Mar. 20, 2007

(54) CAPTURE AND DETECTION FORMAT VERSATILITY FOR DIPSTICK ASSAYS

(75) Inventors: Helen Lee, Cambridge (GB); Hsiang Yun Hu, Union City, CA (US); Magda Anastassova Dineva, Cambridge (GB)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 355 days.

(21) Appl. No.: 10/332,131

(22) PCT Filed: Jul. 6, 2001

(86) PCT No.: PCT/GB01/03029

§ 371 (c)(1),
(2), (4) Date: Apr. 7, 2003

(87) PCT Pub. No.: WO02/04669

PCT Pub. Date: Jan. 17, 2002

(65) Prior Publication Data

US 2004/0053255 A1 Mar. 18, 2004

(30) Foreign Application Priority Data

Jul. 7, 2000 (GB) ................................. 0016833.6

(51) Int. Cl.
C12Q 1/68 (2006.01)
C07H 21/02 (2006.01)
C07H 21/04 (2006.01)
(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| 4,751,177 | A | | 6/1988 | Stabinsky | 435/6 |
|---|---|---|---|---|---|
| 4,868,105 | A | | 9/1989 | Urdea et al. | 435/6 |
| 5,310,650 | A | * | 5/1994 | McMahon et al. | 435/6 |
| 5,645,801 | A | * | 7/1997 | Bouma et al. | 422/68.1 |
| 5,681,697 | A | | 10/1997 | Urdea et al. | 435/6 |
| 5,736,327 | A | | 4/1998 | Collins et al. | 435/6 |
| 5,747,248 | A | | 5/1998 | Collins et al. | 435/6 |
| 6,821,770 | B1 | * | 11/2004 | Hogan | 435/287.2 |

FOREIGN PATENT DOCUMENTS

| EP | 0198662 | 10/1986 |
|---|---|---|
| GB | 2169403 | 7/1986 |
| WO | WO93/13221 | 7/1993 |
| WO | WO94/06940 | 3/1994 |
| WO | WO95/20677 | 8/1995 |
| WO | WO95/27081 | 10/1995 |

OTHER PUBLICATIONS

The Stratagene Catalog, p. 39 (1988).*

* cited by examiner

Primary Examiner—Ethan Whisenant
(74) Attorney, Agent, or Firm—Proskauer Rose LLP

(57) ABSTRACT

Dipsticks for testing for the presence of a target nucleic acid in a sample solution are described the dipsticks comprise a universal capture probe immobilised at a capture zone of the dipstick. The universal capture probe is capable of hybridising to a hook capture probe which is hybridised to the target nucleic acid in the sample solution. A contact end of the dipstick is contacted with the sample solution to cause hook capture probe hybridised to the target nucleic acid to move by capillary action to the capture zone where the target nucleic acid can be detected. Use of the universal and hook capture probes allows dipsticks to be prepared which can be used to capture any target nucleic acid, thereby simplifying preparation of the dipsticks. Specificity of target nucleic acid capture is then achieved by use of an appropriate hook capture probe. Methods and kits are also described.

38 Claims, No Drawings

CAPTURE AND DETECTION FORMAT VERSATILITY FOR DIPSTICK ASSAYS

This application is a 371 of PCT/GB01/03029 on Jul. 6, 2001, which is hereby incorporated by reference.

The present invention relates to improved nucleic acid detection by dipsticks. Dipsticks of the invention are used to detect the presence of a target nucleic acid in a sample solution, for example to identify whether a patient is infected with a disease causing microorganism such as *Chlamydia trachomatis* (CT).

Some conventional tests for detecting the presence of a target nucleic acid in a sample solution rely on amplification of the target nucleic acid using the Polymerase Chain Reaction (PCR). Whilst this reaction allows detection of small quantities of target nucleic acid, it can take several hours before a result is obtained. This can be a significant disadvantage because it is often desired to obtain the result as quickly as possible, for example, to keep patient waiting times to a minimum. Further disadvantages of such methods are the requirement for expensive specialist equipment to perform the reaction and the relatively high cost of the reagents.

In contrast, dipsticks can detect unamplified target nucleic acid without the requirement for any specialist equipment and the results can be obtained much more rapidly than PCR-based methods. The patient can then be treated in the same visit. This is particularly advantageous where the patient is unlikely to, or cannot, return at a later date.

In a typical conventional dipstick described in U.S. Pat. No. 5,310,650, a single stranded DNA capture probe is immobilised on a nitrocellulose filter at a capture zone remote from one end of the filter (the contact end) Sequence of the capture probe is complementary to the sequence of a first region of the target nucleic acid to be detected. A labelled single stranded DNA detection probe is immobilised on the nitrocellulose filter at a probe zone located between the capture zone and the contact end of the filter. The detection probe has sequence complementary to the sequence of a second region (distinct from the first region) of the target nucleic acid.

To detect target DNA in a sample solution thought to contain target DNA, the contact end of the nitrocellulose filter is contacted with the sample solution. The sample solution wicks up the filter by capillary action and passes the probe is zone and the capture zone. As the sample solution passes the probe zone, it mobilises the detection probe and causes it to rise with the sample solution towards the capture zone. Mobilised detection probe can then hybridise to the second region of any target DNA present in the sample solution.

When the hybridised detection probe and target DNA arrive at the capture zone, the first region of the target DNA can hybridise to the immobilised capture probe. A ternary complex is thereby formed between the target nucleic acid, the capture probe and the labelled detection probe. Presence of label at the capture zone, therefore, indicates that target DNA is present in the sample solution.

With a second type of conventional dipstick, the labelled DNA detection probe is not immobilised on the nitrocellulose filter. Instead the detection probe is added to the sample solution under conditions allowing hybridisation of the detection probe to any target nucleic acid in the sample solution. The contact end of the nitrocellulose filter is then contacted with the sample solution and as the sample solution wicks up the dipstick, target nucleic acid which is hybridised to the detection probe rises up the nitrocellulose filter and may be captured at the capture zone by the capture probe.

A disadvantage of the conventional dipstick detection methods described above is that the capture probe hybridises specifically to the target nucleic acid, so a different dipstick with immobilised capture probe must be prepared for each different target nucleic acid to be detected. Similarly, the labelled detection probe hybridises specifically to the target nucleic acid, so a different labelled detection probe must be prepared for each different target nucleic acid to be detected.

According to the invention there is provided use of a hook capture probe capable of hybridising to the target nucleic acid and a universal capture probe capable of hybridising to the hook capture probe in a dipstick assay for testing for the presence of a target nucleic acid in a sample solution.

The term "dipstick assay" as used here means any assay using a dipstick in which sample solution is contacted with the dipstick to cause sample solution to move by capillary action to a capture zone of the dipstick thereby allowing target nucleic acid in the sample solution to be captured at the capture zone by the universal and hook capture probes and detected at the capture zone.

According to a first aspect of the invention there is provided a method for testing for the presence of target nucleic acid in a sample solution which comprises:

a) providing a chromatographic strip having a contact end for contacting the sample solution and a universal capture probe immobilised at a capture zone of the chromatographic strip remote from the contact end;

b) providing a hook capture probe capable of hybridising to a first region of the target nucleic acid and to the universal capture probe;

c) providing a detection probe capable of attaching to the target nucleic acid thereby allowing direct or indirect detection of the target nucleic acid utilising the detection probe;

d) incubating the sample solution with the detection probe under conditions for attachment of the detection probe to target nucleic acid in the sample solution; and incubating the sample solution with the hook capture probe under conditions for hybridisation of the hook capture probe to the first region of target nucleic acid in the sample solution;

e) contacting the sample solution with the contact end of the chromatographic strip so that a complex formed between the hook capture probe, the detection probe and target nucleic acid can travel by capillary action to the capture zone and bind to the capture zone by interaction between the hook capture probe of the complex and the universal capture probe immobilised at the capture zone; and f) checking for the presence of detection probe at the capture zone.

Such methods allow use of the same chromatographic strips to capture different target nucleic acids, simply by use of a hook capture probe specific for the target nucleic acid.

The detection probe and the hook capture probe may be incubated with the sample solution in any order or they may be added to the sample solution at the same time.

A probe may be incubated with the sample solution by simply contacting it with the sample solution if that is sufficient to allow hybridisation to take place.

According to the first aspect of the invention there is also provided a dipstick for testing for the presence of target nucleic acid in a sample solution which comprises a chromatographic strip having:

a contact end for contacting the sample solution;

a universal capture probe immobilised at a capture zone of the chromatographic strip remote from the contact end, the universal capture probe being capable of hybridising to a hook capture probe bound to a first region of the target nucleic acid; and a detection moiety releasably immobilised at a conjugate zone of the chromatographic strip between the contact end and the capture zone, the detection moiety being capable of binding by non base pairing interaction to a detection probe hybridised to a second region of the target nucleic acid.

According to the first aspect of the invention there is also provided a kit for testing for the presence of target nucleic acid in a sample solution which comprises:

i) a dipstick comprising a chromatographic strip with a contact end for contacting the sample solution, and a universal capture probe immobilised at a capture zone of the chromatographic strip remote from the contact end;

ii) a hook capture probe capable of hybridising to a first region of the target nucleic acid and to the universal capture probe; and iii) a detection probe capable of attaching to the target nucleic acid thereby allowing direct or indirect detection of the target nucleic acid utilising the detection probe.

Instead of being incubated with the sample solution, the hook capture probe may be releasably immobilised to the chromatographic strip between the contact end and the capture zone. This may be achieved simply by spotting a solution of the hook capture probe onto the chromatographic strip and allowing it to dry. Thus, several chromatographic strips can be prepared each with the same universal capture probe immobilised at the capture zone. Before a chromatographic strip is used to detect a particular target nucleic acid, it is prepared by releasably immobilising the appropriate hook capture probe to the chromatographic strip to allow capture of that target nucleic acid. Preparation of the chromatographic strips in this way is easier than preparing a chromatographic strip with a capture probe specific to the target nucleic acid by permanently immobilising the capture probe to the chromatographic strip.

According to a second aspect of the invention there is provided a method for testing for the presence of target nucleic acid in a sample solution which comprises:

a) providing a chromatographic strip having a contact end for contacting the sample solution, a universal capture probe immobilised at a capture zone of the chromatographic strip remote from the contact end, and a hook capture probe hybridised to the universal capture probe, the hook probe being capable of hybridising to a first region of the target nucleic acid;

b) providing a detection probe capable of attaching to the target nucleic acid thereby allowing direct or indirect detection of the target nucleic acid utilising the detection probe;

c) incubating the sample solution with the detection probe under conditions for attachment of the detection probe to target nucleic acid in the sample solution;

d) contacting the sample solution with the contact end of the chromatographic strip so that target nucleic acid attached to the detection probe can travel by capillary action to the capture zone and bind to the capture zone by interaction between the hook capture probe immobilised at the capture zone and the first region of the target nucleic acid; and e) checking for the presence of detection probe at the capture zone.

According to the second aspect of the invention there is also provided a dipstick for testing for the presence of target nucleic acid in a sample solution which comprises a chromatographic strip having:

a contact end for contacting the sample solution;

a universal capture probe immobilised at a capture zone of the chromatographic strip remote from the-contact end; and a hook capture probe hybridised to the universal capture probe and which is capable of hybridising to a first region of the target nucleic acid.

According to the second aspect of the invention there is further provided a kit for testing for the presence of target nucleic acid in a sample solution which comprises:

i) a dipstick comprising a chromatographic strip with a contact end for contacting the sample solution, a universal capture probe immobilised at a capture zone of the chromatographic strip remote from the contact end, and a hook capture probe hybridised to the universal capture probe, the hook capture probe being capable of hybridising to a first region of the target nucleic acid; and ii) a detection probe capable of attaching to the target nucleic acid thereby allowing direct or indirect detection of the target nucleic acid utilising the detection probe.

Several chromatographic strips can be prepared each with the same universal capture probe immobilised at the capture zone. Before a chromatographic strip is used to detect a particular target nucleic acid, it is prepared simply by hybridising the appropriate hook capture probe to the universal capture probe to allow capture of that target nucleic acid. Again, preparation of the chromatographic strips in this way is easier than preparing a chromatographic strip with a capture probe specific to the target nucleic acid by permanently immobilising the capture probe to the chromatographic strip.

The detection probe may be capable of attaching to the target nucleic acid by covalent or non covalent attachment. Preferably the detection probe comprises a nucleic acid or nucleic acid analogue capable of attaching to the target nucleic acid by hybridising to a second region of the target nucleic acid.

The detection probe may be coupled to a label thereby allowing direct detection of target nucleic acid utilising the detection probe. Preferably, however, the detection probe allows indirect detection of target nucleic acid by a detection moiety capable of binding to the detection probe when the detection probe has hybridised to the target nucleic acid.

When the detection probe comprises a nucleic acid or nucleic acid analogue, the detection moiety may comprise an antibody or antibody fragment which is capable of binding to the duplex formed between the detection probe and the target nucleic acid when the detection probe has hybridised to the target nucleic acid.

Preferably, however, the detection moiety is a ligand binding moiety and the detection probe comprises a probe coupled to a detection ligand which can be bound by the detection moiety. When the detection probe comprises a detection ligand, the detection moiety may be a non antibody or, preferably, an antibody or antibody fragment.

Preferably the detection ligand comprises biotin and the detection moiety comprises an anti-biotin antibody, or the detection ligand comprises fluorescein and the detection moiety comprises an anti-fluorescein antibody, or the detection ligand comprises 2,4-dinitrophenol (DNP) and the detection moiety comprises an anti-DNP antibody.

Alternatively, the detection ligand may comprise biotin and the detection moiety may comprise avidin, streptavidin, or a derivative thereof which retains biotin binding activity.

The detection moiety may be releasably immobilised at a conjugate zone located between the contact end and the capture zone of the chromatographic strip so that the detection moiety is released and can bind to the detection probe as the detection probe travels by capillary action to the capture zone.

Preferably the detection moiety comprises a label allowing indirect detection of target nucleic acid utilising the detection probe. However, a labelled binding moiety capable of binding the detection moiety bound to the detection probe may instead be used to indirectly detect target nucleic acid.

The label of the detection probe or the detection moiety is preferably non radioactive. More preferably the label is a is colour label, for example a textile dye, a metal sol such as colloidal gold, or coloured particles such as coloured latex particles.

The detection probe may comprise one or more probes. For example, the detection probe may comprise a hook detection probe capable of hybridising to the second region of the target nucleic acid and a universal detection probe capable of hybridising to the hook detection probe when the hook detection probe has hybridised to the target nucleic acid.

When the detection probe comprises a universal detection probe and a hook detection probe, the detection ligand or the label of the detection probe should be coupled to the universal probe.

If the detection probe comprises a single probe coupled to a detection ligand, a different probe must be coupled to the detection ligand each time it is desired to detect a different target nucleic acid or a different region of the same target nucleic acid. Use of a universal detection probe coupled to a detection ligand in conjunction with a hook detection probe is particularly advantageous because the same universal detection probe coupled to the detection ligand can be used with different hook detection probes to detect different target nucleic acids or different regions of the same target nucleic acid. Thus, only one type of probe coupled to the detection ligand needs to be prepared.

According to the invention there is also provided use of a hook detection probe capable of hybridising to the target nucleic acid and a universal detection probe capable of hybridising to the hook detection probe in a dipstick assay for testing for the presence of a target nucleic acid in a sample solution.

The term "dipstick assay" as used here means any assay using a dipstick in which sample solution is contacted with the dipstick to cause sample solution to move by capillary action to a capture zone of the dipstick thereby allowing target nucleic acid in the sample solution to be captured at the capture zone and detected utilising the hook and universal detection probes.

According to a third aspect of the invention there is provided a method for testing for the presence of target nucleic acid in a sample solution which comprises:

a) providing a chromatographic strip having a contact end for contacting the sample solution and a capture probe immobilised at a capture zone of the chromatographic strip remote from the contact end, the capture probe being capable of hybridising to a first region of the target nucleic acid;

b) providing a hook detection probe capable of hybridising to a second region of the target nucleic acid;

c) providing a universal detection probe capable of hybridising to the hook detection probe when the hook detection probe has hybridised to the second region of the target nucleic acid, thereby allowing direct or indirect detection of target nucleic acid utilising the universal detection probe;

d) incubating the sample solution with the hook detection probe and the universal detection probe under conditions for hybridisation of the hook detection probe to the second region of the target nucleic acid and for hybridisation of the universal detection probe to the hook detection probe;

e) contacting the sample solution with the contact end of the chromatographic strip so that a complex formed between the universal detection probe, the hook detection probe and target nucleic acid can travel by capillary action to the capture zone and bind to the capture zone by interaction between target nucleic acid of the complex and the capture probe immobilised at the capture zone; and f) checking for the presence of universal detection probe at the capture zone.

According to the third aspect of the invention there is also provided a kit for testing for the presence of target nucleic acid in a sample solution which comprises:

i) a dipstick comprising a chromatographic strip with a contact end for contacting the sample solution, and a capture probe immobilised at a capture zone of the chromatographic strip remote from the contact end, the capture probe being capable of hybridising to a first region of the target nucleic acid;

ii) a hook detection probe capable of hybridising to a second region of the target nucleic acid; and iii) a universal detection probe capable of hybridising to the hook detection probe when the hook detection probe has hybridised to the second region of the target nucleic acid, thereby allowing direct or indirect detection of the target nucleic acid utilising the hook and universal detection probes.

Instead of being incubated with the sample solution, the universal detection probe optionally with the hook detection probe may be releasably immobilised to the chromatographic strip between the contact end and the capture zone. The probe is then released into the sample solution as it moves by capillary action to the capture zone.

In other embodiments, the hook detection probe optionally with the universal detection probe may be contacted with the capture zone after the sample solution has been contacted with the contact end of the chromatographic strip to allow target nucleic acid to be captured at the capture zone. This may be achieved by contacting a detection probe solution directly with the capture zone, or by contacting the detection probe solution with the contact end of the chromatographic strip after the sample solution thereby allowing the detection probe(s) to move by capillary action to the capture zone. If the detection probe solution does not contain the universal detection probe, this will need to be bound to the hook detection probe after it has been contacted with the capture zone.

Alternatively, if the hook detection probe is incubated with the sample solution or releasably immobilised to the chromatographic strip, the universal detection probe may be contacted with the capture zone after the sample solution has been contacted with the contact end of the chromatographic strip. Again, this may be achieved by directly applying a solution of the universal detection probe to the capture zone or by contacting it with the contact end of the chromatographic strip.

It will be appreciated that hook detection probe must be present in order for universal detection probe to be able to bind to the target nucleic acid.

In other types of dipstick assay, the target nucleic acid may be captured at the capture zone by a capture moiety capable of binding, by non base pairing interaction, to a capture probe hybridised to the target nucleic acid. The capture probe may comprise a ligand which can be bound by the capture moiety. The capture probe is typically prepared by covalently coupling the capture ligand to the part of the capture probe which is capable of hybridising to the target nucleic acid.

Because the capture probe hybridises specifically to the target nucleic acid, a different capture probe with capture ligand must be prepared for each different target nucleic acid to be detected.

Alternatively, where the capture moiety binds by non base pairing interaction directly to the part of the capture probe which is capable of hybridising to the target nucleic acid, a different capture moiety may need to be used each time a different capture probe is used to capture a different target nucleic acid. For example, if the capture moiety is an antibody capable of binding a hybrid formed between the capture probe and the target nucleic acid, the antibody may not have high affinity for all capture probe/target nucleic acid hybrids.

According to a further aspect of the invention there is provided a method for testing for the presence of a target nucleic acid in a sample solution which comprises:

a) providing a chromatographic strip having a contact end for contacting the sample solution and a capture moiety immobilised at a capture zone of the chromatographic strip remote from the contact end, the capture moiety being capable of binding by non base pairing interaction to a universal capture probe bound to the target nucleic acid by a hook capture probe;

b) providing a hook capture probe capable of hybridising to the target nucleic acid;

c) providing a universal capture probe capable of hybridising to the hook capture probe;

d) contacting the sample solution with:
   the hook capture probe under conditions for hybridisation of the hook capture probe to the target nucleic acid; and
   the universal capture probe under conditions for hybridisation of the universal capture probe to the hook capture probe;

e) contacting the sample solution with the contact end of the chromatographic strip so that a complex formed between the universal capture probe, the hook capture probe, and target nucleic acid can travel by capillary action to the capture zone and bind to the capture zone by binding (by non base pairing interaction) of the capture moiety to the capture ligand of the complex; and f) detecting for target nucleic acid at the capture zone.

Preferably the universal capture probe comprises a capture ligand which can be bound by the capture moiety to capture the complex. Examples of suitable capture ligands include biotin, fluorescein and DNP. Biotin can be bound by avidin, streptavidin, or an anti-biotin antibody. Fluorescein and DNP can be bound by anti-fluorescein and anti-DNP antibodies, respectively.

It will be appreciated that different target nucleic acids can be captured simply by using different hook capture probes. Only one type of probe need be prepared coupled to a capture ligand (or capable of being bound by the capture moiety).

The universal and hook capture probes need not be incubated with the sample solution. In other methods, the universal capture probe, optionally with the hook capture probe, may be releasably immobilised to the chromatographic strip between the contact end and the capture zone. Sample solution travelling to the capture zone by capillary action releases the universal capture probe (and the hook capture probe) to allow the released probe(s) to bind to the target nucleic acid. An advantage of releasably immobilising one or more of the probes to the chromatographic strip is that the method is thereby simplified and the number of separate reagents which need to be added to the sample solution is thereby reduced. This can be an important advantage, particularly in remote areas where a dipstick is used to test a sample solution from a patient (such as a urine solution) to determine whether that patient has a particular disease or disorder.

It will be appreciated that if the hook capture probe is not releasably immobilised to the chromatographic strip with the universal capture probe, it should preferably be incubated with the sample solution before the sample solution travels up the chromatographic strip. It is alternatively possible, however, that a separate solution of the hook capture probe could be contacted with the chromatographic strip to cause the hook capture prober solution to travel to the capture zone by capillary action, thereby releasing the universal capture probe and allowing capture of the universal and hook capture probes at the capture zone. The chromatographic strip will then need to be contacted with the sample solution to allow target nucleic acid to be captured by hybridisation of the target nucleic acid to the hook capture probe at the capture zone.

In a further variation of such methods, the universal and hook capture probes could be bound to the capture moiety, for example by directly applying them to the capture zone or by contacting the chromatographic strip with a separate solution of universal and hook capture probe, before the contact end of the chromatographic strip is contacted with the sample solution. Alternatively, the hook capture probe could be releasably immobilised to the chromatographic strip as long as the universal capture probe is bound to the capture moiety before the sample solution is contacted with the contact end.

However, it is preferred that the universal and hook capture probes are added to the sample solution before the sample solution is contacted with the contact end of the chromatographic strip because hybridisation reactions are thought to occur more slowly on the chromatographic strip than non base pairing interactions. The hybridisation conditions can also be more readily controlled if hybridisation is carried out in solution.

There is also provided according to the invention a kit for testing for the presence of a target nucleic acid in a sample solution which comprises:

a dipstick having a chromatographic strip with a contact end for contacting the sample solution and a capture moiety immobilised at a capture zone of the chromatographic strip remote from the contact end, the capture moiety being capable of binding by non base pairing interaction to a universal capture probe bound to the target nucleic acid by a hook capture probe;

a hook capture probe capable of hybridising to the target nucleic acid; and a universal capture probe capable of hybridising to the hook capture probe.

The universal capture probe and/or the hook capture probe may be releasably immobilised to the chromatographic strip between the contact end and the capture zone.

The target nucleic acid may be detected using a detection probe as described previously.

Kits of the invention in which the detection probe or the universal detection probe comprises a detection ligand may further comprise a labelled detection moiety capable of binding to the detection ligand thereby allowing indirect detection of target nucleic acid. The labelled detection moiety may be releasably immobilised to the chromatographic strip between the contact end and the capture zone. There is also provided according to the invention use of a dipstick or kit of the invention to test for the presence of target nucleic acid in a sample solution.

The target nucleic acid may be any nucleic acid, but is preferably nucleic acid of a disease causing micro-organism, more preferably a sexually transmitted disease causing micro-organism. Most preferably the target nucleic acid is *Chlamydia trachomatis* nucleic acid.

In preferred methods of the invention, hybridisation of the probes to target nucleic acid is carried out in the sample solution before the sample solution is contacted with the chromatographic strip (other than hybridisation of the immobilised universal capture probe to the target nucleic acid). Most preferably hybridisation of the probes is carried out in a single step. This simplifies the methods, thereby making them considerably quicker and easier to perform.

Multiple step hybridisation may be carried out by sequential hybridisation of the different probes to the target nucleic acid in the sample solution, or by contacting the chromatographic strip with different solutions each containing a different probe. Usually, the latter method of multiple step hybridisation will involve washing the chromatographic strip between each contact with a different probe solution.

Whilst there may be circumstances in which multiple step hybridisation is preferred, it will be appreciated that the simpler and quicker format of one step hybridisation will usually be preferred.

It is most preferred that the sample solution is of suitable composition to allow the hybridisation reactions to take place in a single hybridisation step and also to allow non base pairing interactions to take place (for example between a detection ligand and a detection ligand binding moiety) and transport a complex comprising target nucleic acid and one or more hybridised probes and (optionally) ligand binding moieties by capillary action up the chromatographic strip.

Using such a sample solution, it will be appreciated that the hybridisation reactions can then be carried out in a single step, and any ligand-ligand binding moiety interactions can take place, before the sample solution is contacted directly with the contact end of the chromatographic strip (without the need to first dilute or alter the sample solution). Ligand-ligand binding moiety interactions can additionally or alternatively take place on the chromatographic strip if desired once the sample solution is in contact with the chromatographic strip. Simple and rapid dipstick detection of target nucleic acid is thereby facilitated.

We have found that such results are achieved with sample solutions comprising a standard hybridisation buffer (such as SSPE buffer or Tris buffer) with salt, detergent and a blocking protein such as BSA or powdered milk. The sensitivity of detection of target nucleic acid using such assays has been found to be about equal to that of other dipstick assays.

Embodiments of the invention are now described by way of example only.

The examples described below relate to detection of *Chlamydia trachomatis* nucleic acid. CT is one of the most common causes of sexually transmitted disease. CT infections can cause infertility and, during pregnancy, can result in spontaneous abortion, still birth or postpartum endometritis. In neonates, CT infection can cause blindness and chronic respiratory disease. Approximately 10% of infected men and up to 70% of infected women do not show symptoms of CT infection. Consequently, accurate diagnosis of CT infection is important so that early treatment of the disease can be initiated.

The sequences of probes used in the following examples are as follows:

```
5'TTC ATA TCC AAG GAC AAT AGA CCA A    SEQ ID NO:1

5'TCC CTC GTG ATA TAA CCT ATC CG       SEQ ID NO:2

5'CAG GTT GTT AAC AGG ATA GCA CGC      SEQ ID NO:3

5'CTC GTT CCG AAA TAG AAA ATC GCA      SEQ ID NO:4

5'GGT AAA GCT CTG ATA TTT GAA GAC      SEQ ID NO:5

5'CTG AGG CAG CTT GCT AAT TAT GAG T    SEQ ID NO:6
```

EXAMPLE 1

CT target nucleic acid (872 bp DNA at $10^{11}$ to $10^8$ copies) was captured using a universal capture probe. The universal capture probe hybridised to a hook capture probe was immobilised to the dipstick. The hook capture probe had sequence complementary to the sequence of the universal capture probe and to the target nucleic acid sequence. Detection was carried out using detection probes of Seq ID No 2, 3, 5 and 6 coupled to biotin at 1012 copies, and an anti-biotin antibody-dye conjugate as a detection moiety. The limit of detection was observed to be $10^9$ copies of target nucleic acid.

EXAMPLE 2

CT target nucleic acid (872 bp DNA at $10^{11}$ and $10^{10}$ copies) was captured using SEQ ID NO: 4 as a capture probe immobilised to the dipstick. Target nucleic acid was detected using a hook detection probe and a universal detection probe. The hook detection probe has sequence corresponding to SEQ ID is NO: 6 (capable of hybridising to the target nucleic acid) and sequence complementary to the sequence of the universal detection probe. The universal detection probe is coupled to a dye allowing detection of the universal detection probe. As few as $10^{10}$ copies of target nucleic acid were detected.

The invention allows simplified preparation of dipsticks and detection probes.

---

The invention claimed is:

1. A dipstick for testing for the presence of a target nucleic acid in a sample solution, wherein the dipstick comprises a chromatographic strip having:
- a contact end for contacting the sample solution;
- a universal capture probe that is immobilized at a capture zone of the chromatographic strip remote from the contact end; and
- a hook capture probe hybridized to the universal capture probe and which is capable of hybridizing to a first region of the target nucleic acid.

2. A dipstick for testing for the presence of a target nucleic acid in a sample solution, wherein the dipstick comprises a chromatographic strip having;
- a contact end for contacting the sample solution;
- a universal capture probe that is immobilized at a capture zone of the chromatographic strip remote from the contact end; and
- a hook capture probe that is releasably immobilized to the chromatographic strip between the contact end and the capture zone, wherein the hook capture probe is capable of hybridizing to a first region of the target nucleic acid, and the universal capture probe is capable of hybridizing to the hook capture probe.

3. The dipstick according to claim 1 further comprises a detection moiety that is releasably immobilized at a conjugate zone of the chromatographic strip between the contact end and the capture zone, wherein the detection moiety is capable of binding by non base pairing interaction to a detection probe that is hybridized to a second region of the target nucleic acid.

4. A dipstick for testing for the presence of a target nucleic acid in a sample solution, wherein the dipstick comprises a chromatographic strip having:
- a contact end for contacting the sample solution;
- a universal capture probe that is immobilized at a capture zone of the chromatographic strip remote from the contact end, wherein the universal capture probe is capable of hybridizing to a hook capture probe bound to a first region of the target nucleic acid; and
- a detection moiety that is releasably immobilized at a conjugate zone of the chromatographic strip between the contact end and the capture zone, wherein the detection moiety is capable of binding by non base pairing interaction to a detection probe hybridized to a second region of the target nucleic acid.

5. The dipstick according to claim 4, wherein the detection moiety comprises a label.

6. The dipstick according to claim 5, wherein the label is non radioactive.

7. The dipstick according to claim 6, wherein the label is a color label.

8. The dipstick according to claim 7, wherein the color label comprises a textile dye, a metal sol, or a colored particle.

9. The dipstick according to claim 4, wherein the detection moiety comprises an antibody or an antibody fragment.

10. The dipstick according to claim 9, wherein the detection moiety comprises an anti-biotin antibody, an anti-fluorescein antibody, or an anti-DNP antibody.

11. The dipstick according to claim 4, wherein the detection moiety comprises avidin, streptavidin, or a derivative thereof which retains biotin binding activity.

12. A dipstick for testing for the presence of a target nucleic acid in a sample solution, wherein the dipstick comprises a chromatographic strip having:
- a contact end for contacting the sample solution;
- a capture probe that is immobilized at a capture zone of the chromatographic strip remote from the contact end, wherein the capture probe is capable of binding directly or indirectly to the target nucleic acid; and
- a universal detection probe that is releasably immobilized to the chromatographic strip between the contact end and the capture zone, wherein the universal detection probe is capable of hybridizing to a hook detection probe.

13. The dipstick of claim 12 further comprises a detection moiety that is releasably immobilized at a conjugate zone of the chromatographic strip between the contact end and the capture zone, wherein the detection moiety is capable of binding by non base pairing interaction to the universal detection probe.

14. A dipstick for testing for the presence of a target nucleic acid in a sample solution, wherein the dipstick comprises:
- a dipstick having a chromatographic strip with a contact end for contacting the sample solution and a capture moiety that is immobilized at a capture zone of the chromatographic strip remote from the contact end, wherein the capture moiety is capable of binding by non base pairing interaction to a universal capture probe bound to the target nucleic acid by a hook capture probe; and
- a hook capture probe or a universal capture probe that is releasably immobilized to the chromatographic strip between the contact end and the capture zone, wherein the hook capture probe is capable of hybridizing to the target nucleic acid, and the universal capture probe is capable of hybridizing to the hook capture probe.

15. The dipstick of claim 1, wherein the target nucleic acid is nucleic acid of a disease causing microorganism, wherein the microorganism is a sexually transmitted disease causing microorganism.

16. The dipstick according to claim 15, wherein the target nucleic acid is *Chlamydia trachomatis* nucleic acid.

17. A method of testing for the presence of a target nucleic acid in a sample solution comprising contacting the dipstick of claim 1 with the sample solution suspected of comprising the target nucleic acid.

18. A kit for testing for the presence of a target nucleic acid in a sample solution, wherein the kit comprises:
i) a dipstick comprising a chromatographic strip with a contact end for contacting the sample solution, and a universal capture probe that is immobilized at a capture zone of the chromatographic strip remote from the contact end; and ii) a hook capture probe capable of hybridizing to a first region of the target nucleic acid and to the universal capture probe.

19. A kit for testing for the presence of a target nucleic acid in a sample solution, wherein the kit comprises:
a dipstick comprising a chromatographic strip with a contact end for contacting the sample solution, a universal capture probe that is immobilized at a capture zone of the chromatographic strip remote from the contact end, and a hook capture probe hybridized to the universal capture probe, wherein the hook probe is capable of hybridizing to a first region of the target nucleic acid.

20. A kit for testing for the presence of a target nucleic acid in a sample solution, wherein the kit comprises:
i) a dipstick comprising a chromatographic strip with a contact end for contacting the sample solution, and a capture probe that is immobilized at a capture zone of the chromatographic strip remote from the contact end, wherein the capture probe is capable of hybridizing to a first region of the target nucleic acid, or is capable of binding indirectly to the target nucleic acid;
ii) a hook detection probe capable of hybridizing to a second region of the target nucleic add; and
iii) a universal detection probe capable of hybridizing to the hook detection probe when the hook detection probe is hybridized to the second region of the target nucleic acid, thereby allowing direct or indirect detection of the target nucleic acid utilizing the detection probe.

21. The kit according to claim 20, wherein the detection probe or the universal detection probe comprises a label thereby allowing direct detection of target nucleic acid utilizing the detection probe or the universal detection probe and the hook detection probes.

22. The kit according to claim 20, wherein the detection probe or the universal detection probe comprises a detection ligand which can be bound by a detection moiety thereby allowing indirect detection of target nucleic acid utilizing the detection probe or the universal detection probe and the hook detection probes.

23. The kit of claim 22 further comprises a detection moiety capable of binding to the detection ligand.

24. The kit of 23, wherein the detection moiety comprises an antibody or an antibody fragment.

25. The kit of 24, wherein the detection ligand comprises a biotin and the detection moiety comprises an anti-biotin antibody, or wherein the detection ligand comprises a fluorescein and the detection moiety comprises an anti-fluorescein antibody, or wherein the detection ligand comprises a 2,4-dinitrophenol (DNP) and the detection moiety comprises an anti-DNP antibody.

26. The kit according to claim 23, wherein the detection moiety is releasably immobilized at a conjugate zone located between the contact end and the capture zone of the chromatographic strip.

27. The kit according to claim 23, wherein the detection moiety comprises a label thereby allowing detection of the detection moiety.

28. The kit according to claim 21, wherein the label is non radioactive.

29. The kit according to claim 28, wherein the label is a color label.

30. The kit according to claim 29, wherein the color label comprises a textile dye, a metal sol, or a colored particle.

31. A kit for testing for the presence of a target nucleic acid in a sample solution, wherein the kit comprises:
a dipstick having a chromatographic strip with a contact end for contacting the sample solution and a capture moiety that is immobilized at a capture zone of the chromatographic strip remote from the contact end, wherein the capture moiety is capable of binding by non base pairing interaction to a universal capture probe bound to the target nucleic acid by a hook capture probe;
a hook capture probe capable of hybridizing to the target nucleic acid; and
a universal capture probe capable of hybridizing to the hook capture probe.

32. A method of testing for the presence of a target nucleic acid in a sample solution using a dipstick assay, wherein the method comprises contacting a dipstick with the sample solution suspected of comprising the target nucleic acid, wherein the dipstick comprises a universal capture probe and a hook capture probe.

33. A method of testing for the presence of a target nucleic acid in a sample solution using a dipstick assay, wherein the method comprises contacting a dipstick with the sample solution suspected of comprising the target nucleic acid, wherein the dipstick comprises a universal detection probe and a hook detection probe.

34. A method of testing for the presence of a target nucleic acid in a sample solution comprising using the kit of claim 18, wherein a dipstick of the kit is contacted with the sample solution suspected of comprising the target nucleic acid.

35. The dipstick of claim 12 further comprises a hook detection probe that is releasably immobilized to the chromatographic strip between the contact end and the capture zone, wherein the hook detection probe is capable of hybridizing to the target nucleic acid.

36. A dipstick for testing for the presence of a target nucleic acid in a sample solution, wherein the dipstick comprises:
a dipstick having a chromatographic strip with a contact end for contacting the sample solution and a capture moiety that is immobilized at a capture zone of the chromatographic strip remote from the contact end, wherein the capture moiety is capable of binding by non base pairing interaction to a universal capture probe bound to the target nucleic acid by a hook capture probe; and
a hook capture probe and a universal capture probe that is releasably immobilized to the chromatographic strip between the contact end and the capture zone, wherein the hook capture probe is capable of hybridizing to the target nucleic acid, and the universal capture probe is capable of hybridizing to the hook capture probe.

37. The kit of claim 18 further comprises a detection probe capable of attaching to the target nucleic acid thereby allowing direct or indirect detection of the target nucleic acid utilizing the detection probe.

38. The kit of claim 19 further comprises a detection probe capable of attaching to the target nucleic acid thereby allowing direct or indirect detection of the target nucleic acid utilizing the detection probe.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: synthetic probe

<400> SEQUENCE: 1
ttcatatcca aggacaatag accaa                                              25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: synthetic probe

<400> SEQUENCE: 2
tccctcgtga tataacctat ccg                                                23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: synthetic probe

<400> SEQUENCE: 3
caggttgtta acaggatagc acgc                                               24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: synthetic probe

<400> SEQUENCE: 4
ctcgttccga aatagaaaat cgca                                               24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: synthetic probe

<400> SEQUENCE: 5
ggtaaagctc tgatatttga agac                                               24

<210> SEQ ID NO 6
<211> LENGTH: 25
<212> TYPE: DNA
<213> ORGANISM: Artificial Sequence
<220> FEATURE:

-continued

```
<223> OTHER INFORMATION: Description of Artificial Sequence: synthetic
      probe

<400> SEQUENCE: 6
ctgaggcagc ttgctaatta tgagt                                            25
```